(12) United States Patent
Myung et al.

(10) Patent No.: US 9,632,057 B2
(45) Date of Patent: Apr. 25, 2017

(54) ULTRA-SENSITIVE GAS SENSORS BASED ON TELLURIUM-SINGLE WALLED CARBON NANOTUBE HYBRID NANOSTRUCTURES

(71) Applicant: THE REGENTS OF THE UNIVERSITY OF CALIFORNIA, Oakland, CA (US)

(72) Inventors: Nosang V. Myung, Riverside, CA (US); Miluo Zhang, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 628 days.

(21) Appl. No.: 14/050,932

(22) Filed: Oct. 10, 2013

(65) Prior Publication Data

US 2014/0103330 A1 Apr. 17, 2014

Related U.S. Application Data

(60) Provisional application No. 61/712,023, filed on Oct. 10, 2012.

(51) Int. Cl.

| | | |
|---|---|---|
| G01N 27/41 | (2006.01) |
| G01N 27/414 | (2006.01) |
| C25D 3/54 | (2006.01) |
| C25D 5/50 | (2006.01) |
| C25D 5/48 | (2006.01) |
| C25D 3/02 | (2006.01) |
| C25D 5/54 | (2006.01) |
| C25D 7/00 | (2006.01) |
| C25D 9/00 | (2006.01) |
| C25D 15/00 | (2006.01) |
| G01N 27/12 | (2006.01) |
| B82Y 15/00 | (2011.01) |
| B82Y 30/00 | (2011.01) |

(52) U.S. Cl.
CPC .......... *G01N 27/4141* (2013.01); *B82Y 15/00* (2013.01); *C25D 3/02* (2013.01); *C25D 3/54* (2013.01); *C25D 5/48* (2013.01); *C25D 5/50* (2013.01); *C25D 5/54* (2013.01); *C25D 7/00* (2013.01); *C25D 9/00* (2013.01); *C25D 15/00* (2013.01); *G01N 27/127* (2013.01); *B82Y 30/00* (2013.01)

(58) Field of Classification Search
CPC ............... G01N 27/406; G01N 27/407; G01N 27/4073; G01N 27/4074; G01N 27/4075; G01N 33/0037
See application file for complete search history.

(56) References Cited

PUBLICATIONS

S. Sen, "Room Temperature Toxic Gas Sensors Based on Tellurium", BARC Newsletter, issue 309, Oct. 2009, p. 135-138.*
T. Siciliano, et al. "Tellurium sputtered thin films as NO2 gas sensors" Sensors and Actuators B: Chemical, vol. 135, 2008, p. 250-254.*

(Continued)

*Primary Examiner* — J. Christopher Ball
(74) *Attorney, Agent, or Firm* — Buchanan Ingersoll & Rooney PC

(57) ABSTRACT

A gas sensor operable at ambient conditions, the sensor includes functionalized feather-like tellurium (Te) nanostructures on single-walled carbon nanotube (SWNTs) networks.

15 Claims, 8 Drawing Sheets

(56) References Cited

PUBLICATIONS

Tsiulyanu, D., et al., "High sensitive tellurium based NO2 gas sensor", Sensors and Actuators B, (2001), pp. 35-39, vol. 73.
Miura, Norio, et al., "High-temperature potentiometric:amperometric NOx sensors combining stabilized zirconia with mixed-metal oxide electrode", Sensors and Actuators B, (1998), pp. 169-178, vol. 52.
Yang, Jiun-Chan, et al., "Compact electrochemical bifunctional NOx/O2 sensor with metal/metal oxide internal reference electrode for high temperature applications", Sensors and Actuators B, Dec. 8, 2007, pp. 448-454, vol. 131.
Penza, M., et al., "NOx gas sensing characteristics of WO3 thin films activated by noble metals (Pd, Pt, Au) layers", Sensors and Actuators B, (1998), pp. 52-59, vol. 50.
Hyodo, T., et al., "Preparation of macroporous SnO2 films using PMMA microspheres and their sensing properties to NOx and H2", Sensors and Actuators B, Mar. 2, 2005, pp. 580-590, vol. 106.
Koshizaki, Naoto, et al., "Sensing characteristics of ZnO-based NO sensor", Sensors and Actuators B, (2000), pp. 119-121, vol. 66.
Elumalai, Perumal, et al., "Sensing Characteristics of YSZ-Based Mixed-Potential-Type Planar NOx Sensors Using NiO Sensing Electrodes Sintered at Different Temperatures", Journal of the Electrochemical Society, Jun. 3, 2005, pp. H95-H101, vol. 152, No. 7.
Miura, Norio, et al., "Stabilized zirconia-based sensor using oxide electrode for detection of NO, in high-temperature combustion-exhausts", Solid State Ionics, (1996), pp. 1069-1073, vol. 86-88.
Zhang, Daihua, et al., "Detection of NO2 down to ppb Levels Using Individual and Multiple In2O3 Nanowire Devices", Nano Letters, Nov. 9, 2004, pp. 1919-1924, vol. 4, No. 10.
Hersam, Mark C., "Progress towards monodisperse single-walled carbon nanotubes", Nature Nanotechnology, Jul. 2008, 387-394, vol. 3, Macmillan Publishers Limited.
Zhang, Ting, et al., "Recent progress in carbon nanotube-based gas sensors", Nanotechnology, Jul. 7, 2008, pp. 1-14 (15 total pages), vol. 19, IOP Publishing Ltd.
Zhang, Wei-De, et al., "Functional hybrid materials based on carbon nanotubes and metal oxides", Journal of Materials Chemistry, (2010), pp. 6383-6391, vol. 20.
Baughman, Ray H., et al., "Carbon Nanotubes—the Route Toward Applications", Science, Aug. 2, 2002, pp. 787-792 (7 total pages), vol. 297.
Kong, Jing, et al., "Nanotube Molecular Wires as Chemical Sensors", Science, Jan. 28, 2000, pp. 622-625 (5 total pages), vol. 287.
Mubeen, Syed, et al., "Palladium Nanoparticles Decorated Single-Walled Carbon Nanotube Hydrogen Sensor", J. Phys. Chem. C, Nov. 4, 2007, pp. 6321-6327, vol. 111, American Chemical Society.
Mubeen, Syed, et al., Sensitive Detection of H2S Using Gold Nanoparticle Decorated Single-Walled Carbon Nanotubes, Analytical Chemistry, Jan. 1, 2010, pp. 250-257, vol. 82, No. 1, American Chemical Society.
Ueda, T. et al., "Preparation of single-walled carbon nanotube/TiO2 hybrid atmospheric gas sensor operated at ambient temperature", Diamond & Related Materials, (2009), pp. 493-496, vol. 18.
Hoa, Nguyen Duc, et al., "Nanowire structured SnOx—SWNT composites: High performance sensor for NOx detection", Sensors and Actuators B, (2009), pp. 253-259, vol. 142.
Sen, Shashwati, et al., "Synthesis of Tellurium Nanostructures by Physical Vapor Deposition and Their Growth Mechanism", Crystal Growth & Design, (2008), pp. 238-242, vol. 8, No. 1, American Chemical Society.
Liu Jian-Wei, et al., "Mesostructured Assemblies of Ultrathin Superlong Tellurium Nanowires and Their Photoconductivity", J. Am. Chem. Soc., Jun. 14, 2010, pp. 8945-8952, vol. 132.
Chaudhuri, B., et al., "Thermoelectric Power of Tellurium Films", Thin Solid Films, pp. 217-223, vol. 82.
Sen, Shashwati, et al., "Chlorine gas sensors using one-dimensional tellurium nanostructures", Talanta, (2009), pp. 1567-1572, vol. 77.
Xiao, Feng, et al., "Electrodeposition of PbTe thin films from acidic nitrate baths", Electrochimica Acta, Aug. 2, 2006, pp. 1101-1107, vol. 52.
Fan, Yuwei, et al, "Identifying and counting point defects in carbon nanotubes", Nature Materials, Dec. 2005, pp. 906-911, vol. 4, Nature Publishing Group.
Kazaoui, S., et al., "Electrochemical tuning of electronic states in single-wall carbon nanotubes studied by in situ absorption spectroscopy and ac resistance", Applied Physics Letters, May 28, 2001, pp. 3433-3735 (4 total pages), vol. 78, No. 22.
Liang, Fengxia, et al., "Synthesis of tellurium nanowires and their transport property", Materials Chemistry and Physics, (2009), pp. 523-526, vol. 113, Elsevier B.V.
Xiangfeng, Duan, et al., "Indium phosphide nanowires as building blocks for nanoscale electronic and optoelectronic devices", Nature, Jan. 4, 2001, pp. 66-69, vol. 409, Macmillan Magazines Ltd.
Star, Alexander et al., "Gas Sensor Array Based on Metal-Decorated Carbon Nanotubes", J. Phys. Chem. B, Apr. 10, 2006, pp. 21014-21020, vol. 110, American Chemical Society.
Lim, Jae-Hong, et al., "Electrical and Sensing Properties of Single-Walled Carbon Nanotubes Network: Effect of Alignment and Selective Breakdown", (2010), pp. 99-105, vol. 22, No. 1, Wiley-VCH Verlag GmbH&Co. KGaA, Weinheim.
Siciliano, Maria, et al., "Single-crystalline Te microtubes: Synthesis and NO2 gas sensor application" Sensors and Actuators B, Aug. 8, 2009, pp. 185-190, vol. 142, Elsevier B.V.
Tsiulyanu, D. et al., "Characterization of tellurium-based films for NO2 detection", Thin Solid Films, May 17, 2005, pp. 252-256, vol. 485, Elsevier B.V.
Kauffman, Douglas R., et al., "Carbon Nanotube Gas and Vapor Sensors", Angew. Chem. Int. Ed., (2008), pp. 3550-6570, vol. 47, Wiley-VCH Verlag GmbH & Co. KGaA, Weinheim.

* cited by examiner

| Structures | Lowest Detection Limit (ppm) | Sensitivity (% ppm⁻¹) | Response time $\tau_{75}$ at 100 ppb (min) | Recovery time $\tau_{50}$ (min) | Operating temp. (°C) |
|---|---|---|---|---|---|
| Te thin film[1] | 0.1 | -20 | ~ | 2.5 | RT |
| Te micro-tubes[30] | 10 | -0.25 | ~ | 5 | RT |
| SWNT (this work) | < 0.1 | -6.4 | 6.6 | 84 | RT |
| This work | 0.05 | -230.0 | 0.6 | 4.4 | RT |

FIG. 11

ULTRA-SENSITIVE GAS SENSORS BASED ON TELLURIUM-SINGLE WALLED CARBON NANOTUBE HYBRID NANOSTRUCTURES

CROSS REFERENCE TO RELATED APPLICATION(S)

This application claims priority under 35 U.S.C. §119(e) to U.S. provisional application No. 61/712,023, filed on Oct. 10, 2012, the entire contents of which is incorporated herein by reference in its entirety.

FIELD

The disclosure relates to a gas sensor, and more particularly, to an ultra-sensitive gas sensor based on tellurium-single walled carbon nanotube hybrid nanostructures.

BACKGROUND

One-dimensional nanostructure based chemiresistive sensors have received great attention because of their compact design and excellent sensing performance including high sensitivity, low detection limits, low power consumption, and ability to integrate multi-sensor arrays. However, these sensors can suffer from slow response and recovery times when it operated at ambient conditions because of slow catalytic or absorption/desorption processes. The sensors can overcome these obstacles by operating at high temperature, which can increase device complexity with higher power consumption rate.

Over the past few decades, the detection of nitrogen dioxide ($NO_2$) in combustion exhaust or in the environment has been of significant interest because the presence of $NO_2$ has been correlated to the formation of acid rain, photochemical smog and some respiratory diseases including emphysema and bronchitis. Several types of $NO_2$ sensors have been developed including chemiresistive, potentiometric, and amperometric, based on metal oxides (for example, $WO_3$, $SnO_2$, ZnO, NiO and $ZrO_2$). Within the realm of gas sensing, chemiresistive metal oxide sensors have dominated the field because of their robust nature and simple circuit design. However, metal oxide based sensors can require high operating temperature in order to obtain decent sensitivities and faster response/recovery times. This feature can significantly reduce selectivity as many analytes interact with oxide surface, while also increasing power consumption and device complexity. In fact, temperature control systems can overshadow both operating costs and design of the actual sensing element and have been the focus of several nanostructured gas sensor platforms, which have demonstrated advanced thermal control architectures through a series of lithographical fabrication steps. Consequently, facile approaches to rapid, reversible and selective chemical detection at room temperature can provide substantial gains in terms of cost and manufacturability to facilitate massive deployment or smart sensor arrays essential for environmental monitoring and medical diagnosis.

SUMMARY

In accordance with an exemplary embodiment, a gas sensor operable at ambient conditions is disclosed, the sensor comprising: feather-like tellurium (Te) nanostructures functionalized on single-walled carbon nanotube (SWNTs) networks.

In accordance with an exemplary embodiment, a method of fabricating a gas sensor is disclosed, the method comprising: electrodepositing tellurium (Te) nanostructures on aligned single-walled carbon nanotubes (SWNTs).

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

FIG. 11 shows a table of a comparison of sensing properties of Te thin film, microtubes, SWNTs, and Te feather like-SWNT hybrid nanostructures counterparts.

DETAILED DESCRIPTION

Figure 1:
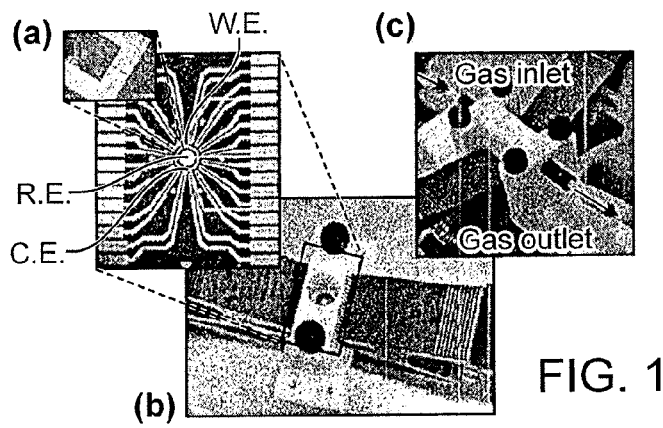
FIG. 1 shows a sensor configuration, which includes (a) Sensor arrays with 15 platinum (Pt) microelectrodes as working electrodes (W.E.), integrated Pt reference electrode (R.E.) and counter electrode (C.E.); (b) Teflon cell with pin SOIC test clips for SWNT alignment and functionalization; and (c) Teflon sensing cell with gas inlet and outlet.

One-dimensional (1-D) nanostructures, such as nanowires and nanotubes have received great attention for fabrication of gas sensors due to their unique size-dependent properties. For example, there has been growing interest in carbon nanotubes (CNTs) owing to their unique electrical, physical, mechanical and chemical properties to develop devices with simplicity, reliability, reproducibility, and low cost. Various electronic devices including supercapacitors, electrodes, field emission devices, and sensors have been synthesized based on single carbon nanotubes, carbon nanotube networks or carbon nanotube films.

SWNT based chemiresistors/chemical field effect transistors (ChemFETs) have been widely used as gas sensors due to their sensitivity to charge transfer and chemical doping effect by various gaseous molecules. However, pristine SWNT based gas sensors have limitations such as low sensitivity to some analytes, lack of selectivity as well as long response and recovery times that hinder their use as stand-alone sensing elements. Therefore, effort has been devoted to surface functionalization of SWNT to modify the sensor properties. The incorporation of typical metal or metal oxide catalysts such as Pd, Au, $TiO_2$ and $SnO_2$ for enhancement of both sensitivity and selectivity toward analyte gases have been discussed. Furthermore, reports have demonstrated improved performance at lower operating temperatures with respect to their thin film counterparts.

Tellurium is a p-type semiconductor with band gap energy of 0.35 eV at room temperature. Tetragonal-Te (t-Te) due to its hexagonal crystal structure that contains six spiral chains in the corner and one in the center. Based on its unique lattice structure, t-Te shows some interesting properties such as photoconductivity, thermoelectric effect, and catalytic activity and has been used in various devices such as thin film transistors, infrared detectors, and gas sensors. For example, polycrystalline Te thin films fabricated by vacuum thermal evaporation can be used as promising $NO_2$ sensors at room temperature. Moreover, Te nanotubes and nanorods made from vacuum or atmospheric thermal evaporation has been reported to detect $Cl_2$, NO and other gases. These Te based sensors exhibited ppm range sensitivity to various gases with response times of around several minutes at room temperature.

In accordance with an exemplary embodiment, Te nanostructure decorated SWNT devices were synthesized by electrodeposition of Te nanostructure on aligned SWNTs. Linear sweep voltammetry (LSV) was utilized to understand the electrochemistry and Te growth. Tunable Te morphologies, including porous beaded structures, needle or blade like geometries, rice shaped particles and extended feather growths, were demonstrated through control over the electrolyte concentration, applied potential and deposition charge density. Decorated SWNT devices were challenged with $NO_2$ gas and the sensing performance was correlated to the Te nanostructure. In accordance with an exemplary embodiment, highly faceted Te feather structures yielded the highest sensitivity with a room temperature $ppb_v$ detection limit with fast rapid response/recovery times. Selectivity of the nanosensors was also demonstrated by measuring its response towards various gases such as $NH_3$, $H_2S$, $H_2$ and $H_2O$.

In accordance with an exemplary embodiment, Pt microelectrodes for 15 sensor arrays were fabricated via a photolithography process. Si wafer with 300 nm of oxidation layer was applied as the substrate (FIG. 1a). Within the sensor arrays, integrated Pt counter and reference electrodes were surrounded by sensor electrodes, which avoided the need to introduce external reference and counter electrodes during the sensor fabrication. Pre-fabricated chips were then cleaned with nanopure water and acetone for future use. A customized Teflon cell was used to hold the chip and locate the solution for the SWNT AC dielectrophoretic alignment and functionalization. The electrical connection between the external electronic equipment and the chip was obtained by clipping the chip with two 32 pin SOIC test clips purchased from Pomona Electronics.

The carbon nanotube suspension was prepared by adding 0.2 mg of commercially available carboxylated single-walled carbon nanotubes (SWNTs, Carbon Solution, Inc. Riverside, Calif.) in 20 mL of N,N-dimethylformamide (DMF, Sigma Aldrich, Mo.), followed by sonicating the contents for 90 minutes until a uniform suspension was obtained. The suspension was then centrifuged at 15000 RPM for 90 min and the supernatant was subsequently collected. Afterwards, 200 µL of the supernatant was placed into the Teflon cell with chip held for SWNT alignment (FIG. 1 b). To obtain optimized SWNT alignment, a 2 peak to peak voltage ($V_{pp}$) and 4 MHz frequency was applied to the electrodes for 4 seconds. A Labview program was designed to command the Keithley 3390 AC generator (aligner) and custom-made DAQ switcher for sequential SWNT alignment. The synthesized sensors were rinsed with nanopure water, dried with ultra-pure $N_2$ gas and then annealed at 300° C. for 2 hours in forming gas.

SWNT functionalization was carried out by the electrodeposition of Te from an acidic nitric bath containing $HTeO_2^+$. In accordance with an exemplary embodiment, the effects of tellurium precursor concentration, applied potential as well as charge density on the morphology and the electrical properties of the Te-SWNT hybrid nanostructures was investigated. The concentration effect was examined by applying 500 µL solutions of 0.1, 1 and 10 mM $HTeO_2^+$ (99+%, Acros Organics) in 1 M nitric acid (Certified ACS Plus, Fisher Chemical) to the system. In accordance with an exemplary embodiment, the deposition potential and charge density were maintained at −1 V and 18.9 mC/cm², respectively. The effect of deposition potential was investigated by varying the potential from −0.8 to −1.4 V with the same charge density applied. Finally, the charge density was varied from about 1.89 to 189 mC/cm² at −1 V to study the influence of charge density on the morphology of deposited Te. After deposition, the sensors were rinsed with nanopure water and dried with nitrogen gas.

Morphologies and compositions of the obtained hybrid Te decorated SWNTs were investigated using field emission-scanning electron microscopy (FE-SEM, Leo model II 1550, Peabody, Mass.) and energy-dispersive X-ray spectroscopy (EDX). Back-gated FET properties were measured by sweeping the gate voltage from −20 V to 20 V while fixing the source-drain potential at 1 V. Furthermore, the sensing performance of the Te-SWNT hybrid structure was studied by installing the sensing chip in a sealed Teflon sensing cell with gas inlet and outlet ports for gas flow and then clipping the chip to a Keithley 236 source measurement to obtain electrical connection (FIG. 1 c). A power supply of 1 V was provided to each sensor and the resistance was continuously recorded every 15 seconds for the fifteen sensors by a LabView program. $NO_2$, $NH_3$, $H_2S$ and water vapor were first diluted in dry air, and then introduced into the Teflon cell at a total gas flow of 200 sccm for gas sensing measurements.

Figure 2:
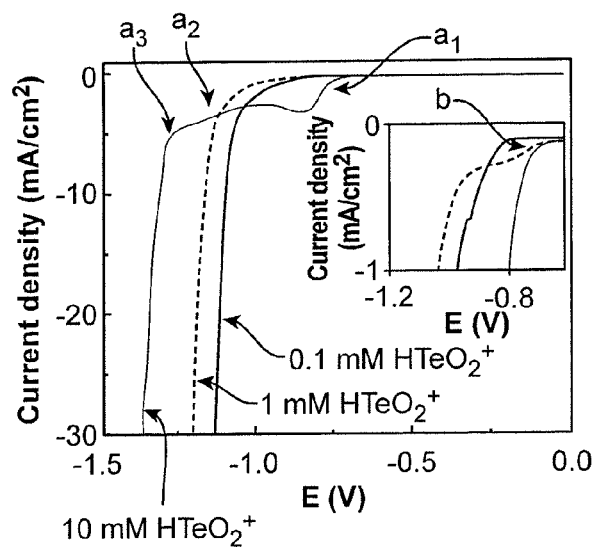
FIG. 2 shows a Linear Sweep Voltammetry (LSV) of Te deposition on SWNT. Electrolytes consisted of 0.1, I, or 10 mM $HTeO_2^+$ in 1M $HNO_3$. Total solution volume was fixed at 500 µL, and wherein the Linear Sweep Voltammetries (LSVs) were performed with a fixed scan rate of 10 mV/s.

The effect of $HTeO_2^+$ concentration, applied potential and charge density on the Te growth was investigated with both Linear Sweep Voltammetry (LSV) and scanning electron microscopy of Te nanostructure deposits. FIG. 2 shows LSV of Te deposition on SWNTs using electrolytes with different concentrations of $HTeO_2^+$. The electrode potential was swept from 0 to −1.4 V vs. a pseudo Pt electrode at a rate of about 10 mV/s. Three reduction waves ($a_1$, $a_2$, and $a_3$) were observed at −0.75 V, −1.1 V and −1.28 V from an electrolyte containing 10 mM $HTeO_2^+$ where $a_1$ may be attributed to reduction of $HTeO_2^+$ to Te (Eq. (2)) and $a_2$ may be attributed to a two-step reduction which involves the electrochemical reduction $HTeO_2^+$ to $H_2Te$ (Eq. (2)) followed by the chemical deposition of Te from $HTeO_2^+$ and $H_2Te$ (Eq. (3)), and wherein $a_1$ is attributed to hydrogen evolution.

$$HTeO_2^+ + 3H^+ + 4e^- \rightarrow Te + 2H_2O$$

$$E^O = +0.551 \text{ V versus NHE} \quad \text{(Eq. 1)}$$

$$HTeO_2^+ + 5H^+ + 6e^- \rightarrow H_2Te(aq) + 2H_2O$$

$$E^O = 0.121 \text{V versus NHE} \quad \text{(Eq. 2)}$$

$$2H_2Te + HTeO_2^+ \rightarrow 2H_2O + H^+$$

$$G_f^0 = -498.118 \text{Kj mol}^{-1} \quad \text{(Eq. 3)}$$

The effects of $HTeO_2^+$ concentration on Te electrodeposition was examined by conducting LSV with various of $HTeO_2^+$ concentration from 0.1 to 10 mM (FIG. 2). As shown in FIG. 2, the electrodeposition potential shift was more cathodic with decreasing the $HTeO_2^+$ concentration of Te. For example, no obvious reduction peak was observed for 0.1 mM $HTeO_2^+$. Finally, as the $HTeO_2^+$ concentration increased the onset of hydrogen evolution can be shown to move to more cathodic potentials as expected due to the 0.551 V difference in reduction potential, which was observed in the case of 10 mM $HTeO_2^+$.

Figure 3:
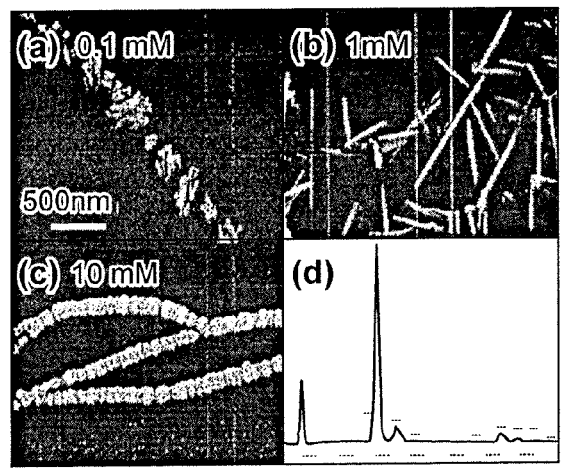
FIG. 3 shows the effect of concentration of $HTeO_2^+$ on the morphology of the Te-SWNT hybrid nanostructure at a fixed applied potential of −1 V and fixed charge density of 18.9 $mC/cm^2$: (a) 0.1 mM; (b) 1 mM; and (c) 10 mM.

In accordance with exemplary embodiment, the effect of electrolyte concentration on the morphology of Te grown potentiostatically at −1 V is shown in FIG. 3 with a fixed deposition charge density of 18.9 mC/cm². The lowest concentration of Te (e.g., 0.1 mM) produced porous and somewhat jagged Te nanoparticles which may result from the competition between limited $HTeO_2^+$ reduction and the dominating hydrogen evolution reaction (HER). These particles result from diffusion limited deposition, consistent with a negligible reduction peak in the LSV, with the growth being quickly quenched by hydrogen reduction. Needle or blade-like Te nanostructures were obtained from a low Te deposition rate when an electrolyte of 1 mM $HTeO_2^+$ concentration was used, owing again to the limitations of mass transfer and mitigated hydrogen evolution with respect to 0.1 mM $HTeO_2^+$ as observed in the inset of FIG. 2. The highly faceted structures and incomplete SWNT coverage can suggest the dendrite growth occurs first by instantaneous nucleation followed by diffusion limited growth, permitting extended structure growth by the smaller HER current, equivalent to that of the Te partial current. Larger Te particles that grow perpendicularly along the SWNTs were observed with the utilization of an electrolyte of higher concentration where HER was insignificant. The rice like appearance can be attributed to instantaneous nucleation followed by three dimensional growths that can be limited laterally by coalescence with neighboring Te grains creating a shell of oblate or scalene ellipsoids due to the underlying substrate. The EDX spectrum (FIG. 3d) identifies the main elemental components as O, Si, Pt and Te, where the former elements are from the silicon substrate and Pt electrodes.

Figure 4:
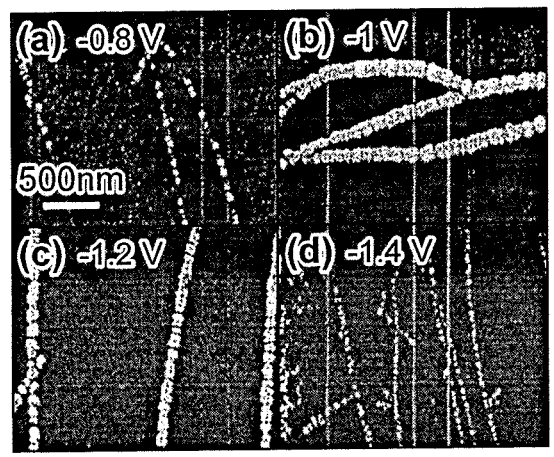
FIG. 4 shows the effect of applied potential on the morphology of the Te-SWNT hybrid nanostructure at a fixed $HTeO_2^+$ concentration of 10 mM and fixed charge density of 18.9 $mC/cm^2$: (a) −0.8 V; (b) −1 V; (c) −1.2 V; (d) −1.4 V.

Morphologies of Te nanoparticles obtained at different deposition potentials but with a fixed charge density (18.9 mC/cm²) and $HTeO_2^+$ concentration (10 mM) are shown in FIG. 4. Small and dispersed Te nanoparticles were nucleated on SWNTs at low potentials (−0.8 V vs. pseudo Pt), indicating that nucleation was mostly taking place at: the SWNT defect sites.

Furthermore, the disparity in particle size can suggest a progressive nucleation mechanism, which would be consistent with defect site mediated nucleation and growth at low overpotentials. A slightly more negative deposition potential, −1 V, produced SWNTs covered with coalesced rice-like Te nodules described above. For example, at more cathodic potentials, −1.2 V, both the size and coverage of the deposits decreased, which would be attributable to HER and the formation $H_2Te$ according to the Eq. (3). The slightly more spherical shape of these particles can also be a consequence of these parasitic reactions and the resulting decreased Te nucleation and growth. In accordance with an exemplary embodiment, hydrogen evolution reaction (HER) was expected to be quite significant when the applied potential reached −1.4 V, leading to the drastically decreased deposition efficiency and size diminution of Te particles.

Figure 5:
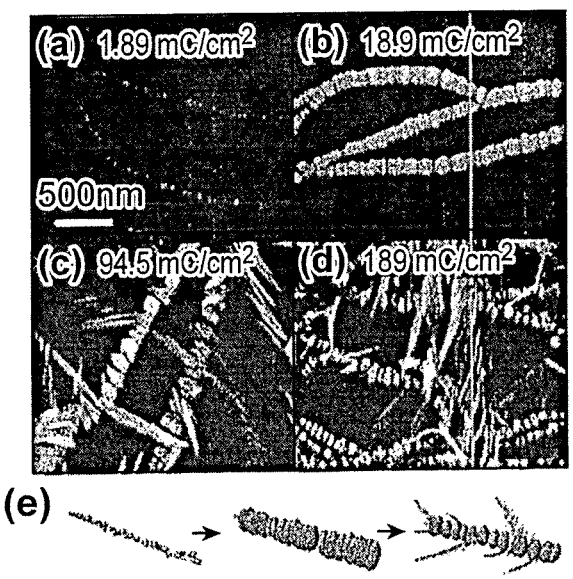
FIG. 5 shows the effect of charge density on the morphology of the Te-SWNT hybrid nanostructure at a fixed $HTeO_2^+$ concentration of 10 mM and controlled applied potential of −1 V. (a) 1.89 $mC/cm^2$; (b) 18.9 $mC/cm^2$; (c) 94.5 $mC/cm^2$; (d) 189 $mC/cm^2$; and (e) Schematic illustration of Te nanostructure growth on SWNTs with increasing charge density.

For example, control over the size, shape and density of the deposits can also be achieved by varying the applied charge density. Small particles (approximately 20 nm) first nucleated along the SWNTs (FIG. 5a) and grew radially to the point of coalescence, thereafter proceeding as ellipsoids to approximately 100 nm along the major axis when the charge density was increased to approximately 18.9 mC/cm². The formation of Te rice-like structures, as observed in FIG. 5b and similarly FIG. 3c, are actually oblate or scalene ellipsoids primarily due to the high nucleation density and panicle coalescence described above. As higher charge (94.5~189 mC/cm²) passed through SWNTs, gaps in the nodules appeared as the size of the particles decreased and feather-like structure immersed from these openings (FIGS. 5c and 5d). In contrast to the incomplete coverage observed at more cathodic potentials due to increased HER (FIG. 4c, d), the decreased size with increasing charge density is progressive meaning the particles reach a maximum size and begin to shrink as more time or charge is passed. This type of growth can be reconciled by chemical etching of particles after establishment of the double layer. Once the mass transfer limited dendritic feather growth occurs, as observed in FIG. 5c, the etching attacks the grain boundaries opening up regions of the SWNT. As more time passes (FIG. 5d) the particles continue to decrease in size as diffusion limited Te can only be deposited on the extended feather dendrites and the highly concentrated acid continues to etch away at the Te beads. For example, FIG. 5e demonstrates the schematic growth of Te nanostructures with increasing charge density under mass transport control.

Figure 6:
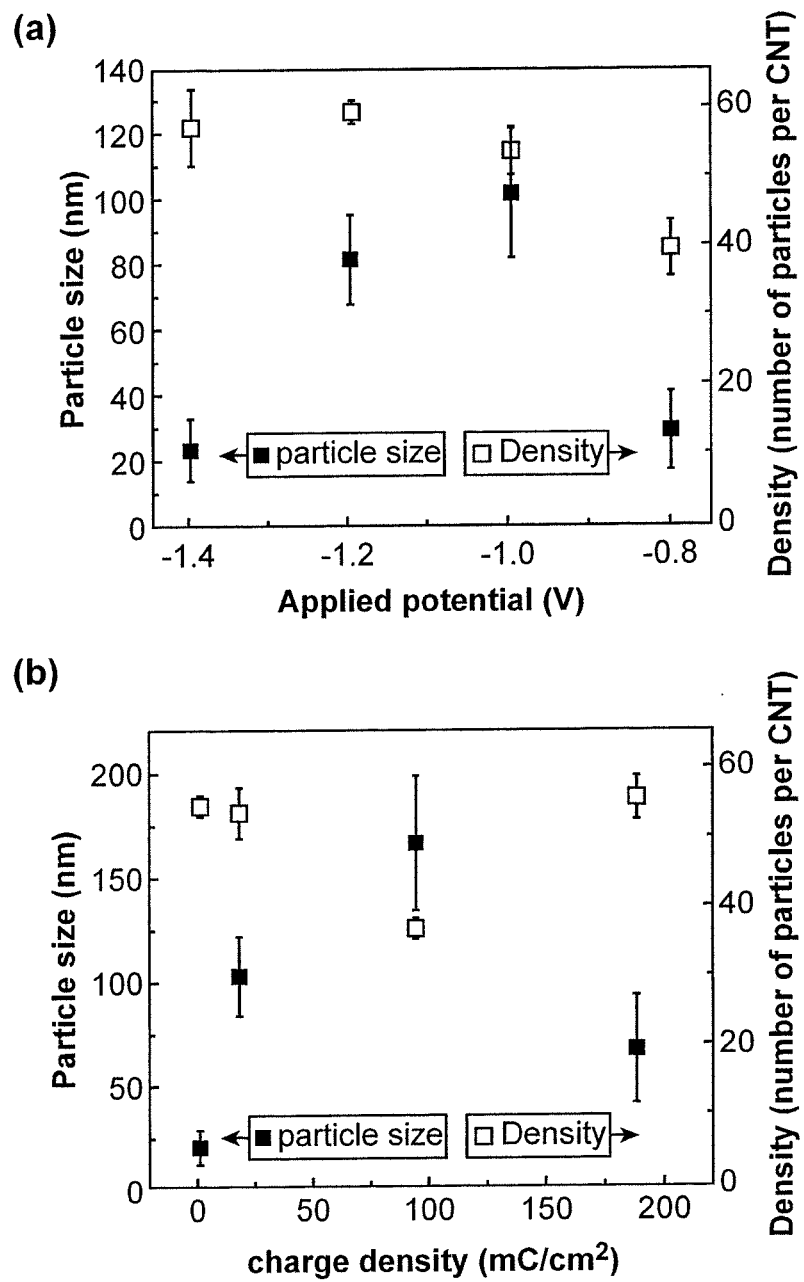
FIG. 6 shows the effect of (a) applied potential and (b) charge density on particle size and density of Te-SWNT hybrid nanostructure.

Quantitative assessment of the applied potential and charge density on panicle size and number of panicles per SWNT is provided in FIG. 6. As expected, the potential dependent particles size reaches a maximum at −1 V due to kinetically limited growth at more positive potentials and competition with HER at more negative potentials. The density of the particles is greater with more cathodic potentials, below −1.4 V, which is consistent with an instantaneous nucleation mechanism and HER limited growth. The effect of charge density on the deposited particle size and number of particles per SWNT is displayed in FIG. 6b. The particle size can be augmented by charge density up to about 94.5 mC/cm² and decreases thereafter. For example, the particle density can be fairly constant except for an uncharacteristic dip at about 94.5 mC/cm², which likely reflects error due to undistinguishable coalescence of particles. Overall, the results of FIGS. 3 through 6 shows that the morphology and density of as decorated metal structures can be controlled by varying the concentration of electrolyte, applied potential as well as charge density.

Figure 7:
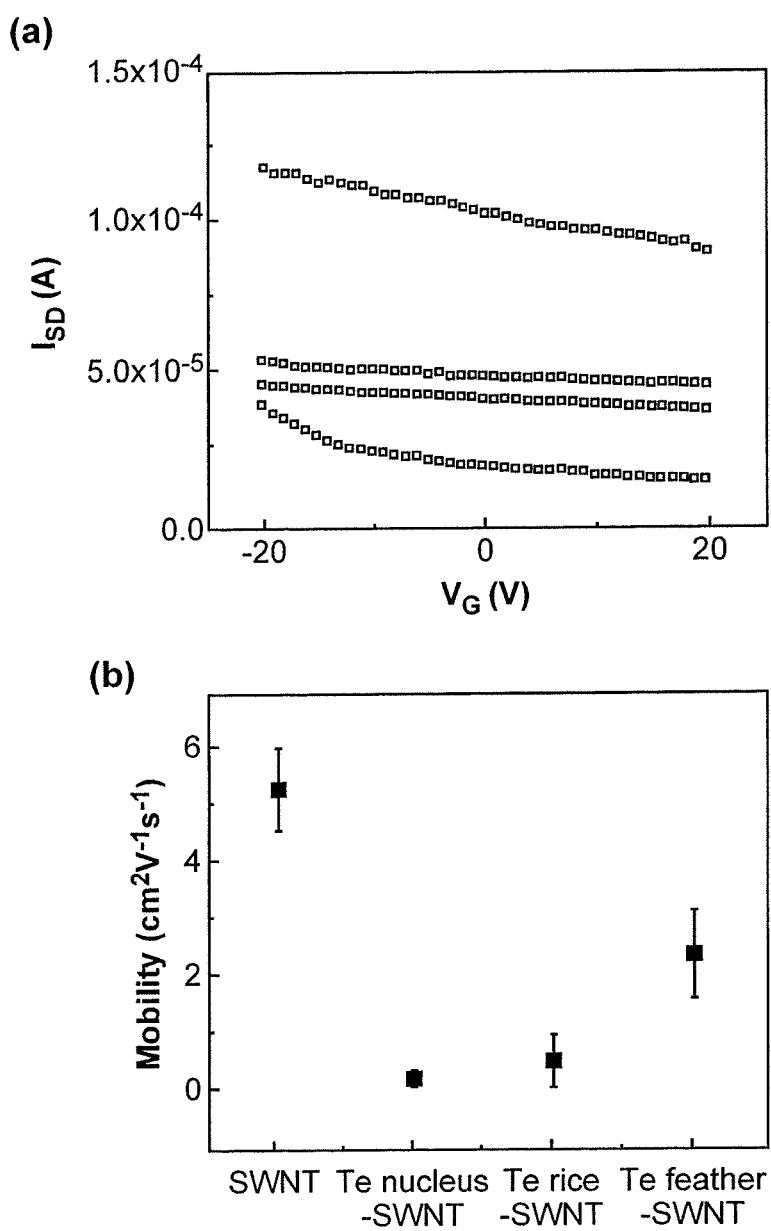
FIG. 7 shows a back-gated field effect transistor (FET) transport properties were measured by sweeping the gate voltage from −20 V to 20 V while fixing the source-drain potential at 1 V, wherein (a) Electron transport properties of AC aligned SWNT and Te-SWNT hybrid nanostructure responses acquired from hybrid structures shown in FIG. 4a, b, and c, respectively, and (b) Carrier mobility of AC aligned SWNT and Te-SWNT hybrid nanostructures.
Figure 8:
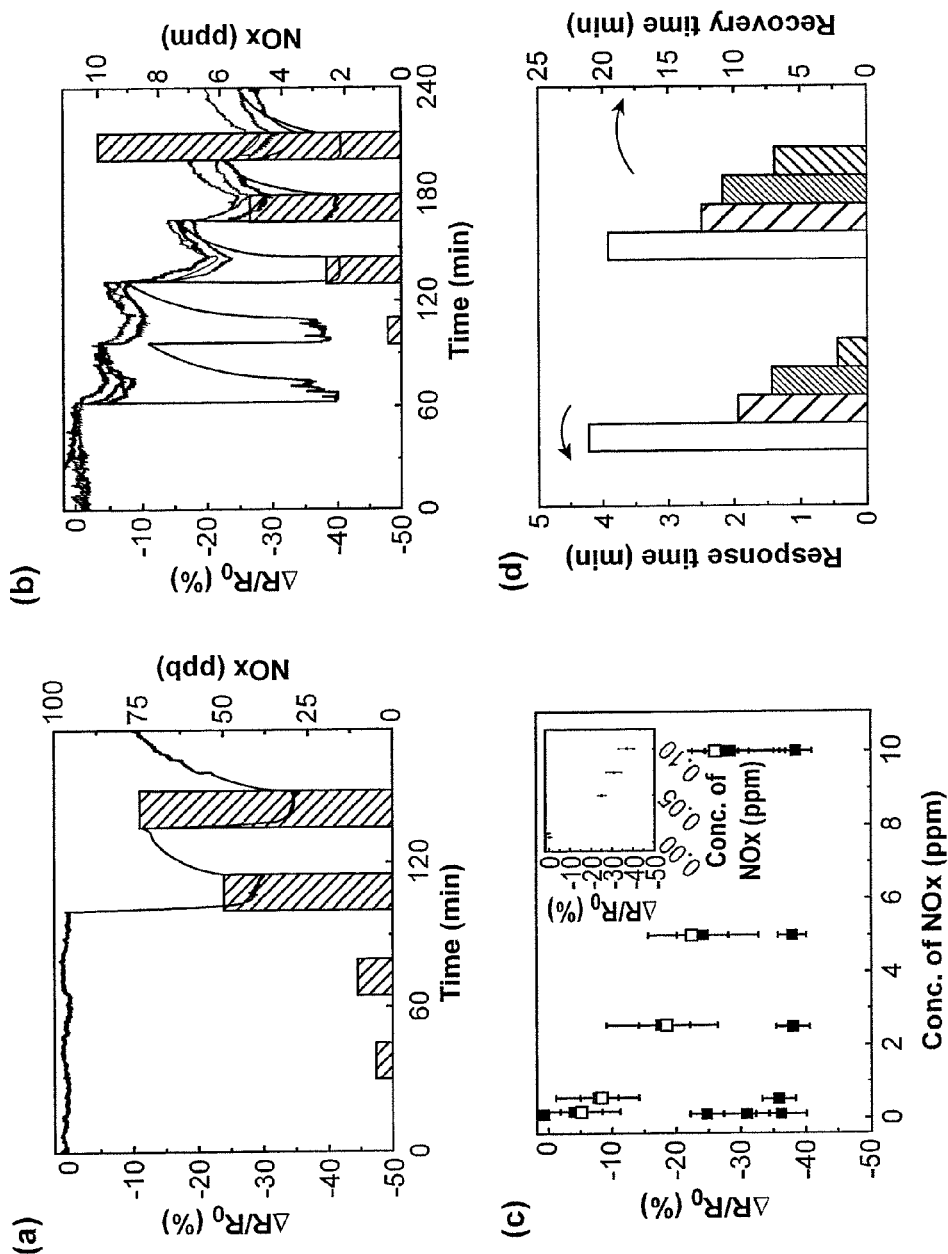
FIG. 8 shows (a, b) Real-time sensing performance, (c) calibration curve, and (d) response and recovery time of AC aligned SWNT and Te-SWNT hybrid nanostructure responses acquired from hybrid structures shown in FIG. 5a, b, and c, respectively, towards $NO_2$ at different concentration.

The room temperature back-gated FET measurements, shown in FIG. 7, were carried out in order to confirm the transfer characteristics of SWNT and the Te-SWNT hybrid nanostructures shown in FIG. 5a, b and c. The source-drain current ($I_{SD}$) versus gate voltage ($V_G$) at fixed voltage ($V_{SD}$) curves were shown in FIG. 7a. All the sensors exhibited p-type semiconducting behavior while deteriorated transport properties were observed after SWNT functionalization, showing neither on nor off values. The conductivity, however, did increase with increased deposition charge and greater Te coverage, doubling that of the SWNT for small Te charge densities and quadrupling for a charge density of 94.5 mC/cm². For example, due to the isotype heterojunction formed between the two p-type semiconductors. The similar small band gaps, 0.57 and 0.35 eV, and work functions, approximately 5.0 eV, for SWNT and Te, respectively, can create small barriers for hole transport between the two materials resulting in parallel current flow through the Te particles, correlating well with the increased conductivity for greater Te coverage and particle diameter. The weakened gate dependence is an expected result of the increased diameter of these hybrid structures as the gate field does not penetrate their cross section as strongly but more importantly the small grain sizes of the Te particles disrupt highly conductive channel formation.

In accordance with an exemplary embodiment, FIG. 6b displays the diminished mobility of Te-SWNT hybrid structures, which reflects the dominant flow along Te particles and its interruption from limited Te grain size. This is consistent with increased particle size and coverage observed in FIG. 5 with the increases mobility in FIG. 7b. Moreover the low hole mobility and high conductivities of these hybrid structures can also be in agreement with the Te dominated conduction mechanism as the high carrier concentration of Te with respect to SWNT permits the observed conductivities. For example, significant mobility enhancement of Te feather-SWNT sensors can result from the charge flow through the Te-SWNT networks by feather bridging and the improved crystallinity associates with these dendritic Te nanostructures.

Sensing responses of the bare SWNT network and three topographically different (FIG. 5a, b and c) Te-SWNT nanosensors towards $NO_2$ at room temperature were investigated with custom system described previously. These sensors were challenged with concentrations of $NO_2$ ranging from 100 $ppb_V$ to 10 $ppm_V$ with 15 minute expose and recovery rimes and the transient are shown in FIG. 7a. The sensor response was determined by the resistance change and defined as $(R_f - R_0)/R_0 \times 100\%$ and is shown in FIG. 5b as a function of analyte concentration; $R_f$ is the final resistance at 95% of the peak height and $R_0$ is initial baseline resistance prior to analyte exposure. The response time is defined as the time for the sensor to reach 75% of its steady-state value. The recovery time is identified as the time required for the sensor after the exposure to return to 50% of its maximum response. In accordance with an exemplary embodiment, the response and recover times are depicted as a histogram in FIG. 5c with response times ranging from 0.5 to 7 minutes and recovery times ranging 7 to 20 minutes for 100 $ppb_V$ $NO_2$. For example, in nearly all cases Te functionalization improved response/recovery time with respect to the SWNT network. In addition, in terms of sensitivity, the smaller Te charge densities can display near negligible change in performance. SWNTs with Te feather-like structures showed the best sensing performance for all metrics with dramatically higher sensitivity and taster response/recovery rimes, clearly superior to the other devices. Upon exposure to 100 $ppb_V$ $NO_2$, a 40% change in resistance was achieved with response and recovery times of 36 s and 7 min, respectively. The minimum detection limit of $NO_2$ was found to be around 50 $ppb_V$, which is the lowest value for Te based $NO_2$ sensor to date (Insert in FIG. 5c).

Figure 9:
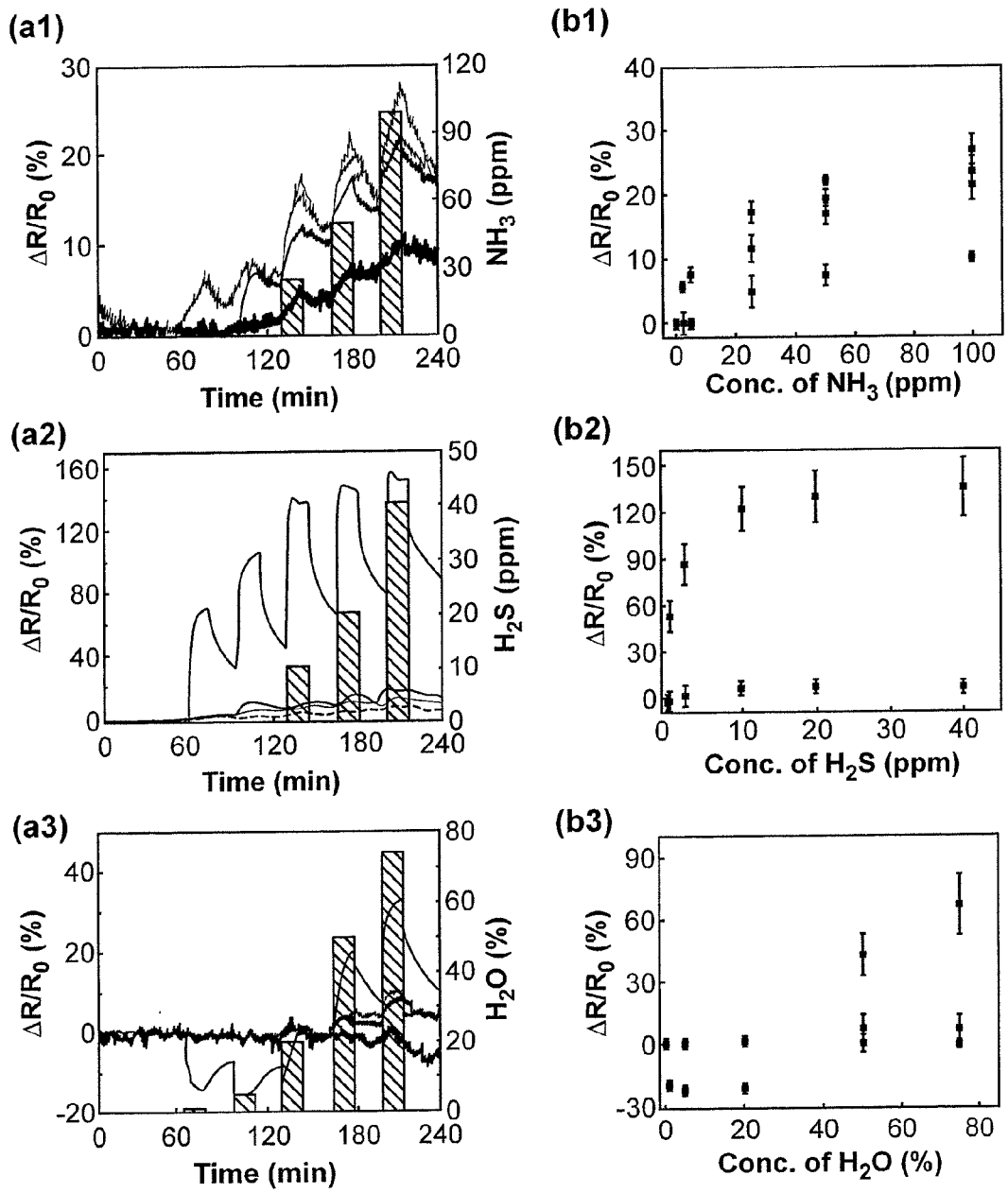
FIG. 9 shows (a) Real-time sensing performance and (b) calibration curve of AC aligned SWNT and Te-SWNT hybrid nanostructure responses acquired from hybrid structures shown in FIG. 5a, b, and c, respectively, towards (1) $NH_3$ (2) $H_2S$ and (3) $H_2O$, and wherein sensing performance towards $H_2$ was not shown here.

In accordance with an exemplary embodiment, these sensors were also challenged with background analytes to identify potential interferences and demonstrate sensor viability in real life conditions. The selectivity of the gas sensors can be determined by analyzing their response to various gases such as $NH_3$, $H_2S$, $H_2$ (not shown) and $H_2O$ vapor (FIG. 9). For example, morphology dependent sensing performance was observed with improved behavior in the Te feather-like structure. For the case of ammonia ($NH_3$), all Te decorated devices displayed similar behavior doubling in sensitivity over that of the SWNT control with greater Te charge density giving the best performance. However, dramatic improvement for these set of analytes was seen for $H_2S$ in which a response of up to 130% was achieved at the PEL level (20 $ppm_V$) with the feather Te nanostructures, almost 10 times higher than the other structures. The response to water was mixed with lower Te loadings providing negligible difference from the SWNT control and the highest Te loading producing mixed responses, from negative to positive resistance changes, depending on concentration suggesting competitive sensing mechanism. While the positive change in resistance to $NH_3$ and $H_2S$ gives little concern for sensor function, the large decrease in resistance at smaller $H_2O$ concentration suggests this device may require a desiccant to dry the air prior to introduction with the sensor.

Figure 10:
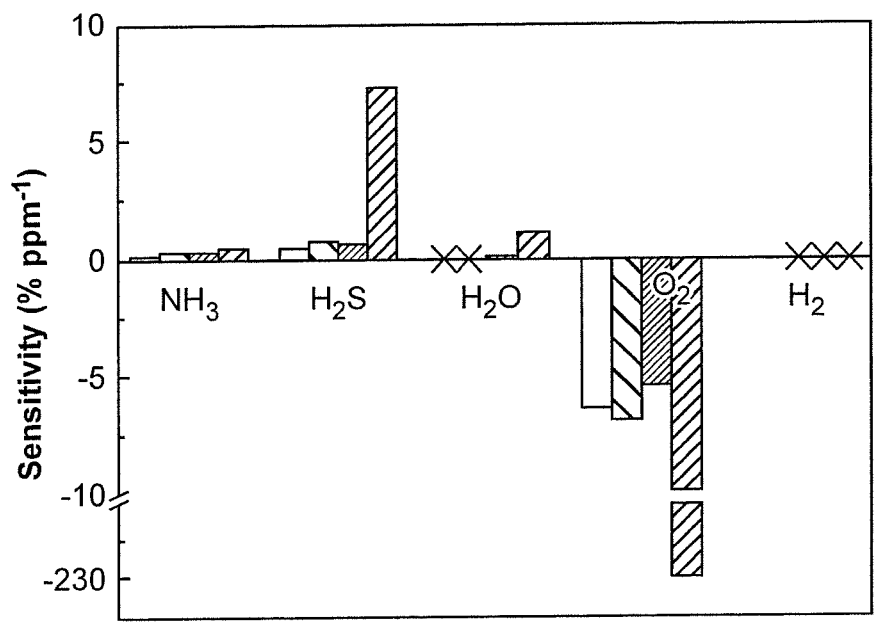
FIG. 10 shows sensitivity of AC aligned SWNT and Te-SWNT hybrid nanostructure responses acquired from hybrid structures shown in FIG. 5a, b, and c, respectively, towards $NH_3$, $H_2S$, $H_2O$, $NO_2$ and $H_2$.

The sensitivities for each sensor to each analyte, as well as $H_2$, can be calculated by taking the slope of the linear part of the sensing calibration curve and compiled in FIG. 10. The combined responses give a unique picture or signature for each analyte by which the system can distinguish an individual gas and assist in quantitative assessment of concentration. Specifically, the direction change in response to $NO_2$ with respect to the other gases provides ease in analyte identification and establishes a means to bypass sample dehumidification. The magnitude of the these sensitivities displays fairly typical or modest values with one notable exception, the Te-SWNT nanostructures showed the highest sensitivity of 230.0% $ppm_V$ towards $NO_2$, which is the highest room temperature sensitivity reported to date (FIG. 11).

In accordance with an exemplary embodiment, the sensing mechanism of the Te and SWNT can be explained by the alteration of the transport properties owing to the interaction of adsorbed species to the SWNT and Te surfaces. As a strong electron acceptor, a $NO_2$ molecule can receive electrons from the valence band of the semiconductors resulting in the enhancement of the hole density in both Te and SWNTs, thus decreasing the resistance. Likewise, when electron donors such as $NH_3$ and $H_2S$ were introduced to the sensor, the hole concentration decreased leading the resistance to increase. The superior sensing performance by the Te feather-like structure can be due to its larger surface-to-volume ratio and increased crystallinity, which provides for its higher conductivity and field effect carrier mobility. For example, this sensor analyte can directly interact with the Te feathers, the carrier super highways of the device, to strongly impact carrier transport. Similar behavior in both transient profile and sensitivity values between SWNT networks and hybrid devices with smaller Te loadings can be a consequence of a SWNT nanotubes dominated resistance. The breaks in Te coverage can be higher resistance sections and hence sensitivity can be derived from exposed SWNT permitting similar results as the SWNT control.

As disclosed herein, a Te-SWNT hybrid nanostructure based $NO_2$ sensor can be synthesized by means of AC dielectrophoretic alignment of SWNT followed by Te electrodeposition. Shape, morphology and size of the Te particles can be controlled by adjusting the electrodeposition conditions and electrolyte composition. Te rice-like and feather-like structures can be synthesized by varying the applied charge density (e.g., 18.9 $mC/cm^2$ and 94.5 $mC/cm^2$) at a fixed applied potential of −1 V, using an electrolyte containing 10 mM of $HTeO_2^+$. Te deposition appears to follow instantaneous nucleation of small panicles along SWNTs followed by the growth of the nucleus to form rice-like structures and finally highly crystalline feather-like structures once mass transfer limitations set in. The gating dependent effects of SWNTs can be diminished upon Te decoration owing to transport though the Te particles and their small grains, but enhanced from transport through Te feather suggesting improved crystallinity in Te feathers.

Sensing results indicated the enhancement of the sensitivity by Te functionalization of SWNTs, for example, by the feather-like Te-SWNT hybrid nanostructures. In accordance with an exemplary embodiment, a $NO_2$ nanosensor can be developed based on Te feather-SWNT structures with a superior selectivity, high sensitivity of 54%/$ppm_v$ and quick response and recovery times of 36 sec and 7 min to 100 $ppb_v$ $NO_2$ at room temperature. The sensing mechanism can be explained by the change in carrier transport properties induced from the adsorption of analytes. The outstanding sensing performance of the Te feather-like SWNT structures can be due to its large surface-to-volume ratio and higher field carrier mobility. The sensors were tested against background analytes to demonstrate viability (min) in the field.

The invention is not limited, however, to the embodiments and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A gas sensor operable at ambient conditions, the sensor comprising:
   feather-like tellurium (Te) nanostructures functionalized on single-walled carbon nanotube (SWNTs) networks; and
   tailoring a morphology and a density of the feather-like Te nanostructures to a response and a recovery time of approximately 36 sec and 7 min to 100 $ppb_v$ $NO_2$ gas at room temperature, respectively.

2. The sensor of claim 1, comprising:
   a silicon wafer substrate configured to receive the functionalized feather-like tellurium (Te) nanostructures on the single-walled carbon nanotube (SWNTs) networks.

3. The sensor of claim 2, comprising:
   a plurality of working electrodes on the silicon wafer substrate; and
   a sensing cell having a gas inlet and a gas outlet.

4. A method of fabricating a gas sensor, the method comprising:
   electrodepositing a tellurium (Te) solution on aligned single-walled carbon nanotubes (SWNTs); and
   controlling deposition charge density during the electrodeposition of the tellurium (Te) solution on the aligned single-walled carbon nanotubes (SWNTs) to form feather-like tellurium (Te) nanostructures.

5. The method of claim 4, comprising:
   preparing a carbon nanotube suspension of carboxylated single-walled carbon nanotubes in a solution of N, N-dimethylformamide;
   sonicating the solution until a uniform suspension is obtained;
   centrifuging the suspension and collecting a supernatant;
   placing the supernatant into a Teflon cell with a chip for SWNT alignment; and
   obtaining alignment of the single-walled carbon nanotubes (SWNTs) across the microelectrodes.

6. The method of claim 5, comprising:
   obtaining alignment by applying 2 peak to peak voltage ($V_{pp}$) and 4 MHz frequency for approximately 4 seconds.

7. The method of claim 6, comprising:
   rinsing the synthesized sensor with nanopure water;
   drying the sensor with ultra-pure $N_2$ gas; and
   annealing the sensor.

8. The method of claim 7, wherein the annealing is at 300° C. for 2 hours in forming gas.

9. The method of claim 4, wherein the electrodeposition of the tellurium (Te) solution comprises:
   electrodepositing Te from an acidic nitric bath containing $HTeO_2^+$.

10. The method of claim 5, comprising:
    rinsing the sensor with nanopure water; and
    drying the sensor with nitrogen gas.

11. The method of claim 5, comprising:
    configuring the sensor to sense nitrogen dioxide ($NO_2$).

12. The method of claim 11, comprising:
    tailoring the morphology and density of the feather-like Te nanostructures to a response and a recovery time of approximately 36 sec and 7 min to 100 $ppb_v$ $NO_2$ gas at room temperature, respectively.

13. The method of claim 4, comprising:
    forming the feather-like tellurium (Te) nanostructures at a charge density of about 94.5 $mC/cm^2$ to about 189 $mC/cm^2$.

14. The method of claim 9, wherein the acidic nitric bath containing $HTeO_2^+$ comprises:
    10 mM (millimolar) of $HTeO_2^+$.

15. The method of claim 9, comprising:
    fixing an applied potential during electrodeposition at −0.75 V to −1.28 V.

* * * * *